United States Patent [19]
Sakyu et al.

[11] Patent Number: 6,166,276
[45] Date of Patent: Dec. 26, 2000

[54] METHOD FOR PRODUCING HEPTAFLUOROPENTANE

[75] Inventors: Fuyuhiko Sakyu; Naoto Takada; Hideaki Imura; Takeo Komata, all of Saitama, Japan

[73] Assignees: Central Glass Company, Limited, Ube; Nippon Zeon Co., Ltd., Tokyo, both of Japan

[21] Appl. No.: 09/449,621

[22] Filed: Nov. 30, 1999

[30] Foreign Application Priority Data

Nov. 30, 1998 [JP] Japan .................................. 10-339419

[51] Int. Cl.⁷ .................................................... C07C 17/10
[52] U.S. Cl. .............................................................. 570/176
[58] Field of Search ............................................. 570/176

[56] References Cited

U.S. PATENT DOCUMENTS 5,416,246  5/1995  Krespan et al. .

FOREIGN PATENT DOCUMENTS 1046095  10/1966  United Kingdom .

*Primary Examiner*—Alan Siegel
*Attorney, Agent, or Firm*—Evenson, McKeown, Edwards & Lenahan, P.L.L.C.

[57] ABSTRACT

The invention relates to a method for producing 1,1,2,2,3,3,4-heptafluorocyclopentane. This method includes the step of reducing 1,1-dichlorooctafluorocyclopentane by hydrogen in the presence of a hydrogenation catalyst. This catalyst contains at least one first metal selected from metals of 8, 9, and 10 groups of periodic table, such as iron, cobalt, palladium, platinum, rhodium, ruthenium, iridium, and osmium. According to this method, it is possible to produce 1,1,2,2,3,3,4-heptafluorocyclopentane with high yield and high selectivity.

15 Claims, No Drawings

METHOD FOR PRODUCING HEPTAFLUOROPENTANE

BACKGROUND OF THE INVENTION

The present invention relates to methods for producing 1,1,2,2,3,3,4-heptafluorocyclopentane, which is a useful compound as refrigerant, foaming agent and solvent.

British Patent Publication 1046095 discloses a hydrogenation of an octafluorocyclopentene by hydrogen at a temperature of 175–200° C. in the presence of a catalyst containing alumina carrying thereon 0.1% palladium. With this, a small amount of 1,1,2,2,3,3,4-heptafluorocyclopentane is obtained together with 1,2-dihydrooctafluorocyclopentane.

SUMMARY OF THE INVENTION

It is therefore an object of the present invention to provide a method for producing 1,1,2,2,3,3,4-heptafluorocyclopentane with high yield and high selectivity.

According to the present invention, there is provided a method for producing 1,1,2,2,3,3,4-heptafluorocyclopentane. This method comprises reducing 1, 1-dichlorooctafluorocyclopentane by hydrogen in the presence of a hydrogenation catalyst that comprises at least one first metal selected from metals of 8, 9, and 10 groups of periodic table. The inventors unexpectedly found that it is possible to obtain 1,1,2,2,3,3,4-heptafluorocyclopentane with high yield and high selectivity by this method.

DESCRIPTION OF THE PREFERRED EMBODIMENTS

In the invention, the method for producing the starting material, 1,1-dichlorooctafluorocyclopentane, is not particularly limited. U.S. Pat. No. 5,416,246 discloses an isomerization of 1,2-dichlorooctafluorocyclopentane in the presence of aluminum chlorofluoride (catalyst), thereby to produce 1,1 - dichlorooctafluorocyclopentane.

As mentioned above, the hydrogenation catalyst comprises at least one first metal selected from metals of 8, 9, and 10 groups of periodic table, such as iron, cobalt, palladium, platinum, rhodium, ruthenium, iridium, and osmium. Of these, palladium is preferable. Thus, the at least one first metal is preferably palladium alone or a combination of palladium (major active component) and at least one other metal of 8, 9, and 10 groups of periodic table.

In the invention, the hydrogenation catalyst may further comprise at least one second metal other than metals of 8, 9 and 10 groups of periodic table. The at least one second metal is selected from silver, copper, gold, tellurium, zinc, chromium, molybdenum, thallium, tin, bismuth, lead, and the like. In fact, the at least one first and second metals may be formed into an alloy. The at least one second metal is in an amount preferably of 0.01–500 parts by weight, more preferably of 0.1–300 parts by weight, relative to 100 parts by weight of the at least one first metal, in order to have a sufficient catalytic effect of the at least one first metal. The hydrogenation catalyst may further comprise a carrier carrying thereon preferably 0.05–10 wt %, more preferably 0.5–5 wt %, of the at least one first metal or the above alloy, based on the weight of the carrier. Preferable examples of the carrier are activated carbon, alumina, zirconia, and titania. The particle size of the carrier almost does not have an influence on the reaction and is preferably from 0.1 to 100 mm.

In the invention, it is possible to greatly vary the ratio of hydrogen to the starting material, 1,1-dichlorooctafluorocyclopentane, in order to reduce 1,1-dichlorooctafluorocyclopentane by hydrogen. In fact, it is preferable to use at least stoichiometric amount of hydrogen relative to 1,1-dichlorooctafluorocyclopentane. It is more preferable to use substantially more than stoichiometric amount, such as 3 moles or more, of hydrogen relative to 1 mol of 1,1-dichlorooctafluorocyclopentane. The reaction pressure can be normal pressure (e.g., atmospheric pressure) or more. The reaction temperature is preferably from 0 to 450° C., more preferably from 50 to 300° C. The reaction is conducted preferably in a liquid or gas phase. In case of the gas phase, the reaction is conducted by bringing hydrogen into contact with 1,1-dichlorooctafluorocyclopentane with a contact time of preferably from 0.1 to 300 seconds, more preferably from 1 to 30 seconds.

The following nonlimitative catalyst preparations are illustrative of the present invention.

CATALYST PREPARATION 1

At first, a 500-ml eggplant-type flask was charged with 100 g of a granular activated carbon made by Takeda Chemical Industries, Ltd. having a trade name of GRANULAR SHIRO SAGI G2X-4/6. Then, about 150 ml of an about 20% nitric acid aqueous solution was added to the flask. After that, the flask was allowed to stand still for about 3 hr, thereby to conduct a nitric acid treatment of the activated carbon. Separately, 2.321 g of bismuth (III) nitrate pentahydrate, $Bi(NO_3)_3 \cdot 5H_2O$, and 200 ml of an about 30% nitric acid aqueous solution were mixed together in a 300 ml beaker. Then, the bismuth nitrate was completely dissolved therein in a water bath, to prepare a bismuth nitrate aqueous solution. Separately, 8.335 g of palladium (II) chloride, $PdCl_2$, was dissolved in 50 g of a 24% hydrochloric acid, to prepare a palladium chloride solution. Then, the bismuth nitrate aqueous solution and the palladium chloride solution were mixed together. The resultant mixture was poured on the activated carbon contained in the flask. Then, this flask was allowed to stand still for 2 days. Then, the activated carbon, impregnated with the mixture, was subjected to vacuum drying with an evaporator by increasing the bath temperature to 150° C. Then, the dried activated carbon was put into a reaction tube having a diameter of 25 mm, an axial length of 400 mm, and a capacity of about 200 ml. Then, while nitrogen was allowed to flow through the reaction tube at a rate of 200–300 ml/min, the reaction tube was heated from 150° C. to 300° C. by increasing the set temperature of the reaction tube stepwise by 50° C., in order to bake the activated carbon. The reaction tube temperature was maintained at 300° C. for 1 hr in order to further bake the same, and then the set temperature was decreased to 150° C. After that, while nitrogen and hydrogen were allowed to flow therethrough at respective rates of 100 ml/min and 300 ml/min, the reaction tube temperature was increased again to 300° C. by increasing its set temperature stepwise by 30° C. for conducting reduction. With this, there was prepared a hydrogenation catalyst A having an activated carbon carrying thereon 5% of palladium and 1% of bismuth, based on the weight of the activated carbon.

CATALYST PREPARATION 2

At first, a 500-ml eggplant-type flask was charged with 100 g of a granular activated carbon which is the same as that of Catalyst Preparation 1. Then, about 150 ml of an about 20% nitric acid aqueous solution was added to the flask. After that, the flask was allowed to stand still for about 3 hr, thereby to conduct a nitric acid treatment of the activated carbon. Separately, 8.335 g of palladium (II) chloride, $PdCl_2$, was dissolved in 50 g of a 24% hydrochloric acid, to prepare a palladium chloride solution. Then, this solution was poured on the activated carbon contained in the flask. Then, this flask was allowed to stand still for 2 days. Then, the activated carbon, impregnated with the palladium chloride solution, was subjected to the same treatments as those of Catalyst Preparation 1. With this, there was prepared a hydrogenation catalyst B having an activated carbon carrying thereon 5% of palladium, based on the weight of the activated carbon.

CATALYST PREPARATION 3

At first, a 300-ml eggplant-type flask was charged with 60 g of a granular activated carbon which is the same as that of Catalyst Preparation 1. Separately, 0.796 g of hexachloroplatinic (IV) acid hexahydrate ($H_2PtCl_6 \cdot 6H_2O$) was dissolved in 100 ml of 30% hydrochloric acid. Then, the obtained solution was poured on the activated carbon contained in the flask. Then, this flask was allowed to stand still for 2 days. Then, the activated carbon, impregnated with the hexachloroplatinic acid solution, was subjected to the same treatments as those of Catalyst Preparation 1. With this, there was prepared hydrogenation catalyst C having an activated carbon carrying thereon 0.5% of platinum, based on the weight of the activated carbon.

CATALYST PREPARATION 4

At first, 0.47 g of $H_2PtCl_6 \cdot 6H_2O$ was dissolved in 40 g of 30% hydrochloric acid in a 200-ml Erlenmeyer flask. Then, 0.175 g of $PdCl_2$ and 60 g of 30% hydrochloric acid were added to the flask, thereby to prepare a homogeneous solution. Separately, a 500-ml eggplant-type flask was charged with 35 g of a granular activated carbon which is the same as that of Catalyst Preparation 1. Then, the solution was poured on the activated carbon contained in the flask. After that, this flask was allowed to stand still for 2 days. Then, the activated carbon, impregnated with the solution, was subjected to vacuum drying with an evaporator by increasing the bath temperature to 150° C. Then, the dried activated carbon was put into a reaction tube having a diameter of 18 mm, an axial length of 440 mm, and a capacity of about 110 ml. Then, while nitrogen was allowed to flow through the reaction tube at a rate of 50 ml/min, the reaction tube was heated from 150° C. to 300° C. by increasing the set temperature of the reaction tube stepwise by 50° C., in order to bake the activated carbon. The reaction tube temperature was maintained at 300° C. for 1 hr in order to further bake the same, and then the set temperature was decreased to 150° C. After that, while nitrogen and hydrogen were allowed to flow therethrough at respective rates of 50 ml/min and 175 ml/min, the reaction tube temperature was increased again to 300° C. by increasing its set temperature stepwise by 30° C. for conducting reduction. With this, there was prepared a hydrogenation catalyst D having an activated carbon carrying thereon 0.5% of platinum and 0.5% of palladium, based on the weight of the activated carbon.

The following nonlimitative examples are illustrative of the present invention.

EXAMPLE 1-1

While nitrogen and hydrogen were allowed to flow at respective rates of 100 ml/min and 340 ml/min through a stainless steel (SUS304) reaction tube charged with 120 ml of the hydrogenation catalyst A of Catalyst Preparation 1, it was started to increase the reaction tube temperature by setting the same to 85° C. This reaction tube had a diameter of 25 mm, an axial length of 400 mm and a capacity of about 200 ml. Separately, 1,1-dichlorooctafluorocyclopentane was vaporized by an organic matter vaporizer that was set to have a temperature of 110° C. This vaporizer was connected to an upper part of the reaction tube and had a diameter of 18 mm and an axial length of 300 mm. When the reaction tube temperature reached the set temperature, 85° C., it was started to introduce the vaporized 1,1-dichlorooctafluorocyclopentane into the reaction tube at a rate of 0.2 g/min. After that, the reaction temperature became stable at 89° C. (see Table). As shown in Table, a produced reaction gas was found by gas chromatography to have a composition of 4.0% 1-chloro-1,2,3,3,4,4,5,5-octafluorocyclopentane (1C8F-CPA), 0.2% 1,1,2,2,3,3,4,5-octafluorocyclopentane (8F-CPA), 92.3% 1,1,2,2,3,3,4-heptafluorocyclopentane (7F-CPA), and 2.7% 1,1,2,2,3,3-hexafluorocyclopentane (6F-CPA). These percentages are areal percentages in chromatogram.

EXAMPLE 1-2

In this example, Example 1-1 was repeated in order to see the reproducibility of the results of Example 1-1. The results of Example 1-2 are also shown in Table.

EXAMPLES 1-3 AND 1-4

In each of these examples, Example 1-1 was repeated except in that the reaction temperature was changed as shown in Table.

EXAMPLE 2-1 AND 2-2

In each of these examples, Example 1-1 was repeated except in that the hydrogenation catalyst A was replaced with the hydrogenation catalyst B and that the reaction temperature was changed as shown in Table. The results are shown in Table.

EXAMPLE 3

In this example, Example 1-1 was repeated except in that the hydrogenation catalyst A was replaced with the hydrogenation catalyst C and that the reaction temperature was changed as shown in Table. The results are shown in Table.

EXAMPLE 4

While nitrogen and hydrogen were allowed to flow at respective rates of 50 ml/min and 175 ml/min through a stainless steel (SUS304) reaction tube charged with 76 ml of the hydrogenation catalyst D of Catalyst Preparation 4, it was started to increase the reaction tube temperature by setting the same to 85° C. This reaction tube had a diameter of 18 mm, an axial length of 440 mm and a capacity of about 110 ml. Separately, 1,1-dichlorooctafluorocyclopentane was vaporized by an organic matter vaporizer that was set to have a temperature of 110° C. This vaporizer was connected to an upper part of the reaction tube and had a diameter of 18 mm and an axial length of 300 mm. When the reaction tube temperature reached the set temperature, 85° C., it was started to introduce the vaporized 1,1-dichlorooctafluorocyclopentane into the reaction tube at a rate of 0.2 g/min. After that, the reaction temperature became stable at 88° C. (see Table). A produced reaction gas was analyzed by gas chromatography. The results are shown in table.

TABLE

| | Hydrogenation Catalyst Type | Temp. (° C.) | Composition (GC %) | | | | | | |
|---|---|---|---|---|---|---|---|---|---|
| | | | 7F-CPE | 1C7F-CPE | 1C8F-CPA | 8F-CPA | 7F-CPA | 6F-CPA | Others |
| Ex. 1-1 | A | 89 | 0.0 | 0.0 | 4.0 | 0.2 | 92.3 | 2.7 | 0.2 |
| Ex. 1-2 | A | 89 | 0.1 | 0.0 | 3.7 | 0.2 | 92.4 | 2.7 | 0.1 |
| Ex. 1-3 | A | 122 | — | — | 0.0 | 0.5 | 93.6 | 4.3 | 0.5 |
| Ex. 1-4 | A | 72 | 0.0 | — | 0.5 | 0.3 | 95.0 | 3.2 | 0.3 |
| Ex. 2-1 | B | 84 | 0.0 | — | 1.4 | 0.2 | 94.0 | 3.4 | 0.3 |
| Ex. 2-2 | B | 123 | — | — | 0.1 | 0.4 | 92.6 | 4.2 | 0.3 |
| Ex. 3 | C | 84 | 8.1 | 68.3 | 3.5 | — | 11.2 | 7.6 | 0.4 |
| Ex. 1 | D | 88 | 0.5 | 0.9 | 4.0 | 0.8 | 86.4 | 4.7 | 0.2 |

7F-CPE: 1,3,3,4,4,5,5-heptafluorocyclopentene
1C7F-CPE: 1-chloro-2,3,3,4,4,5,5-heptafluorocyclopentene
1C8F-CPA: 1-chloro-1,2,3,3,4,4,5,5-octafluorocyclopentane
8F-CPA: 1,1,2,2,3,3,4,5-octafluorocyclopentane
7F-CPA: 1,1,2,2,3,3,4-heptafluorocyclopentane
GF-CPA: 1,1,2,2,3,3-hexafluorocyclopentane The entire disclosure of Japanese Patent Application No. 10-339419 filed on Nov. 30, 1998, of which priority is claimed in the present application, including specification, claims, and summary, is incorporated herein by reference in its entirety.

What is claimed is:

1. A method for producing 1,1,2,2,3,3,4-heptafluorocyclopentane, said method comprising reducing 1,1-dichlorooctafluorocyclopentane by hydrogen in the presence of a hydrogenation catalyst that comprises at least one first metal selected from metals of 8, 9, and 10 groups of periodic table.

2. A method according to claim 1, wherein said hydrogenation catalyst comprises palladium.

3. A method according to claim 2, wherein said hydrogenation catalyst further comprises at least one second metal selected from the group consisting of silver, copper, gold, tellurium, zinc, chromium, molybdenum, thallium, tin, bismuth, and lead.

4. A method according to claim 3, wherein said at least one first and second metals are formed into an alloy.

5. A method according to claim 4, wherein said at least one second metal is in an amount of 0.01 to 500 parts by weight relative to 100 parts by weight of said at least one first metal.

6. A method according to claim 4, wherein said hydrogenation catalyst further comprises a carrier carrying thereon said alloy.

7. A method according to claim 6, wherein said carrier is selected from the group consisting of activated carbon, alumina, zirconia, and titania.

8. A method according to claim 6, wherein said alloy is in an amount of 0.05–10 wt %, based on a weight of said carrier.

9. A method according to claim 1, wherein said hydrogenation catalyst further comprises a carrier carrying thereon said at least one first metal.

10. A method according to claim 9, wherein said carrier is selected from the group consisting of activated carbon, alumina, zirconia, and titania.

11. A method according to claim 9, wherein said at least one first metal is in an amount of 0.05–10 wt %, based on a weight of said carrier.

12. A method according to claim 1, wherein said at least one first metal is selected from iron, cobalt, palladium, platinum, rhodium, ruthenium, iridium, and osmium.

13. A method according to claim 1, wherein said reducing is conducted at a temperature of 0–450° C. in a liquid phase.

14. A method according to claim 1, wherein said reducing is conducted at a temperature of 0–450° C. in a gas phase.

15. A method according to claim 14, wherein said reducing is conducted by bringing said hydrogen into contact with said 1,1-dichlorooctafluorocyclopentane with a contact time of 0.1–300 seconds.

* * * * *